United States Patent
Martinez

(10) Patent No.: US 9,784,431 B2
(45) Date of Patent: Oct. 10, 2017

(54) LIGHT-EMITTING DEVICE WITH DIFFRACTIVE STRUCTURES AND A SYNTHETIC HOLOGRAM

(71) Applicant: COMMISSARIAT A L'ENERGIE ATOMIQUE ET AUX ENE ALT, Paris (FR)

(72) Inventor: Christophe Martinez, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 447 days.

(21) Appl. No.: 14/474,667

(22) Filed: Sep. 2, 2014

(65) Prior Publication Data
US 2015/0062885 A1 Mar. 5, 2015

(30) Foreign Application Priority Data
Sep. 5, 2013 (FR) ...................................... 13 58492

(51) Int. Cl.
| | |
|---|---|
| *G01N 21/3504* | (2014.01) |
| *F21V 7/00* | (2006.01) |
| *F21L 4/02* | (2006.01) |
| *G01N 21/94* | (2006.01) |
| *G01N 33/00* | (2006.01) |

(Continued)

(52) U.S. Cl.
CPC ............. *F21V 7/0008* (2013.01); *F21L 4/02* (2013.01); *G01N 21/3504* (2013.01); *G01N 21/94* (2013.01); *G01N 33/004* (2013.01); *G03H 1/0005* (2013.01); *G03H 1/0841* (2013.01); *G03H 1/2286* (2013.01); *H01L 31/055* (2013.01); *G01N 2201/068* (2013.01); *G03H 1/0244* (2013.01); *G03H 1/0891* (2013.01); *G03H 2001/0212* (2013.01); *G03H 2001/0216* (2013.01); *G03H 2001/0858* (2013.01); *G03H 2001/2226* (2013.01); *G03H 2222/16* (2013.01); *G03H 2222/47* (2013.01); *G03H 2223/16* (2013.01); *Y02E 10/52* (2013.01)

(58) Field of Classification Search
CPC ............................. F21L 4/02; F21V 7/00008
USPC ..... 250/339.13; 359/1, 9, 15, 350, 360, 563, 359/569, 566
See application file for complete search history.

(56) References Cited

U.S. PATENT DOCUMENTS

| | | | | |
|---|---|---|---|---|
| 5,602,657 A | * | 2/1997 | Dickson | G02B 5/32 359/1 |
| 5,719,397 A | * | 2/1998 | Hallett | G01N 21/3504 250/339.13 |

(Continued)

OTHER PUBLICATIONS

U.S. Appl. No. 14/496,332, filed Sep. 25, 2014, Martinez.

(Continued)

*Primary Examiner* — Yara B Green
(74) *Attorney, Agent, or Firm* — Oblon, McClelland, Maier & Neustadt, L.L.P.

(57) ABSTRACT

A light-emitting device including at least a metal layer able to be heated and to propagate surface waves consecutive to the heating of the metal layer, with the metal layer being structured such that it comprises several diffraction patterns able to carry out a diffraction of the surface waves to free-space propagation modes, wherein a synthetic hologram is encoded such that a phase image of a pixel of the hologram is encoded by an offset in the position of one of the diffraction patterns, and a heater of the metal layer.

17 Claims, 8 Drawing Sheets

(51) Int. Cl.
    G03H 1/00      (2006.01)
    G03H 1/08      (2006.01)
    G03H 1/22      (2006.01)
    H01L 31/055    (2014.01)
    G03H 1/02      (2006.01)

(56) References Cited

U.S. PATENT DOCUMENTS

| | | | | |
|---|---|---|---|---|
| 6,278,534 | B1* | 8/2001 | Arns | G01J 3/02 356/334 |
| 6,734,436 | B2* | 5/2004 | Faris | B01L 3/502792 204/450 |
| 6,917,471 | B2* | 7/2005 | Shiozaki | G01J 3/02 359/558 |
| 2001/0003035 | A1* | 6/2001 | Ozarski | G02B 5/1852 430/321 |
| 2004/0252278 | A1* | 12/2004 | Williams | A61B 1/0669 351/221 |
| 2013/0135702 | A1 | 5/2013 | Martinez | |
| 2013/0342884 | A1 | 12/2013 | Martinez | |
| 2015/0355597 | A1* | 12/2015 | Schwerdtner | G02B 5/1876 359/9 |

OTHER PUBLICATIONS

C. B. Burckhardt, "Use of a Random Phase Mask for the Recording of Fourier Transform Holograms of Data Masks", Applied Optics, vol. 9, No. 3, Mar. 1970, pp. 695-700.

A. W. Lohmann et al., "Binary Fraunhofer Holograms, Generated by Computer", Applied Optics, vol. 6, No. 10, Oct. 1967, pp. 1739-1748.

Wai-Hon Lee, Binary Computer-Generated Holograms, Applied Optics, vol. 18, No. 21, Nov. 1, 1979, pp. 3661-3669.

A. Datas et al., "Global Optimization of Solar Thermophotovoltaic Systems", Progress in Photovoltaics: Research and Applications, 2012, 16 pages.

J.J. Greffet, "Controlled Incandescence", Nature, 2011, vol. 478, pp. 191-192.

Ming Li et al., "Optical Waveguide Fan-Out Elements Using Dislocated Gratings for Both Outcoupling and Phase Shifting", IEEE Photonics Technology Letters, vol. 8, No. 9, Sep. 1996, pp. 1199-1201.

J. Le Gall et al., "Experimental and Theoretical Study of Reflection and Coherent Thermal Emission by a SiC Grating Supporting a Surface-phonon Polariton", Physical Review B, vol. 55, No. 15, Apr. 15, 1997, 10 pages.

En-Kuang Tien et al., "Discrete Parametric Band Conversion in Silicon for Mid-infrared Applications", Optics Express, vol. 18, No. 21, Oct. 11, 2010, 9 pages.

E.A. Vinagradov et al., "Thermostimulated Polariton Emission of Zinc Selenide Films on Metal Substrate", Solid State Communications, vol. 23, issue 12, Sep. 1977, pp. 915-921.

French Preliminary Search Report issued Jun. 16, 2014, in Patent Application No. FR 1358492, filed Sep. 5, 2013 (with English Translation of Category of Cited Documents).

Irina Puscasu, et al., "Photonic Crystals Enable Infrared Gas Sensors", Proceedings of SPIE, vol. 5515, XP 055011700, Jan. 2004, pp. 58-66.

Erez Hasman, et al., "Manipulation of Thermal Emission by Use of Micro and Nanoscale Structures", Journal of Heat Transfer, vol. 134, No. 3, XP 009178412, Mar. 2012, pp. 031023-1-031023-7.

F. Marquier, et al., "Coherent spontaneous emission of light by thermal sources", Physical Review B, vol. 69, No. 15, XP 002353244, Apr. 15, 2004, pp. 155412-1-155412-11.

Pierre Barritault, et al., "Mid-IR source based on a free-standing microhotplate for autonomous $CO_2$ sensing in indoor applications", Sensors and Actuators A, vol. 172, No. 2, XP 028336715, Sep. 21, 2011, pp. 379-385.

M. Laroche, et al., "Highly directional radiation generated by a tungsten thermal source", Optics Letters, vol. 30, No. 19, XP 001235370, Oct. 1, 2005, pp. 2623-2625.

* cited by examiner

LIGHT-EMITTING DEVICE WITH DIFFRACTIVE STRUCTURES AND A SYNTHETIC HOLOGRAM

TECHNICAL FIELD

The invention relates to a light-emitting device with diffractive structures wherein a synthetic hologram is encoded, forming a "light-emitting hologram" obtained via the heating of a metal layer wherein the synthetic hologram is encoded. The invention also relates to a gas sensor comprising such a light-emitting device, as well as a photovoltaic device comprising such a light-emitting device.

PRIOR ART

In order to be able to control the quality of the air, there is a need to have inexpensive and reliable detection systems that make it possible to measure low concentrations of volatile organic compounds, carbon monoxide or carbon dioxide. Spectroscopy is a privileged application channel in the field of detecting gases, which uses the spectral signature of the chemical compounds to be detected in order to allow their concentrations to be measured. For example, the absorption spectrum of $CO_2$ comprises in particular a very pronounced peak around 4.25 µm (therefore in the infrared range). A device for detecting $CO_2$ by spectroscopy can therefore detect the presence of this gas via the detection of such an absorption peak in the spectrum of an optical signal that is in the presence of this gas. Its application in low-cost systems remains however problematic and requires implementing components that are energy efficient and easy to mass produce.

The principle of spectroscopic analysis is based on the spectral segmentation of an optical signal. This segmentation is generally carried out by a dispersive element such as a diffraction grating, or a selective element such as a chromatic filter.

A gas sensor that is based on the principle of spectroscopic analysis therefore comprises elements that carry out an emission of an optical signal, a formatting of the optical signal, a zone of interaction between the gas to be detected and the optical signal, a spectral segmentation of the optical signal that has interacted with the gas, and a detection.

In the case of a gas sensor intended to carry out the detection of one or several gases that have absorption peaks in the infrared range (IR), such as for example $CO_2$, the generation of an optical signal in the infrared range can be obtained at least cost by using an incandescent filament. An incandescent filament emits an optical signal linked to the temperature of the filament, this phenomenon is described under the term black body emission. When its temperature increases, a black body emits a more intense optical signal oriented towards the low wavelength region. Detecting a spectral band around 4.25 µm therefore requires a filament heated to the highest temperature possible. This high temperature must however be compatible with the power and ageing constraints required for the proper operation of the sensor.

FIG. 1 diagrammatically shows a gas sensor 10 intended to carry out a detection of $CO_2$. The sensor 10 comprises an infrared light source formed by an incandescent filament 12, for example comprised of tungsten. This incandescent filament 12 comprises a central radiating plate 14 connected to two electrical connection pads 16. Such an infrared source can be made by implementing collective microelectronic methods, as described for example in the document of P. Barritault et al., "Mid-IR source based on a free-standing microhotplate for autonomous $CO_2$ sensing in indoor applications", Sensors and Actuators A: Physical, Volume 172, Issue 2, December 2011, pages 379-385. The incandescent filament 12 emits a radiation according to the black body theory when it is heated at a high temperature, for example to 700° C. The infrared light emission obtained is formatted by a first optic 18 which collimates the light beam in order to direct it towards a chromatic filter 20, then a second optic 22 concentrates the filtered beam onto a detector 24. The filter 20 allows the spectrum detected to be limited to a single spectral band around the wavelength to be detected, i.e. 4.25 µm for $CO_2$.

Using an incandescent filament as a light source for the sensor has the advantage of having low energy consumption and able to be manufactured in great numbers. However, such a sensor 10 requires the use of several optics for formatting the light beam and of a spectral limitation filter due to the fact that the light radiation of the incandescent filament 12 has a broad and isotropic spectrum (the emission does not favour any particular direction).

There are solutions that make it possible to exacerbate a form of selectivity of the radiation emitted by a light source. This selectivity generally implements effects linked to the presence of polaritons which are coupling elements between surface vibrations of the heated material and photons. The presence of polaritons on a material surface does not result in an emission of light because the energy remains localised on the surface of the material, on surface modes. In order to obtain an emission of light, a resonance artifice has to be used, such as for example a prism or a grating. The wave vector of the light can then leave the plane of the surface of the heated material.

The document of F. Marquier et al., "Coherent spontaneous emission of light by thermal sources"; Physical Review B, vol. 69, Issue 15, id. 155412 (2004), describes an infrared light source comprising a periodic grating carried out in a layer of material. This material is heated and irradiated according to the spectrum of the black body formed by this material. The material chosen has the property of allowing the propagation of SPP (Surface Phonon Polaritons) at its interface with the air (polar material). When these guided waves encounter the periodic grating, a coupling phenomenon is produced and energy is transferred in the form of a light wave that propagates through the air coherently in a certain range of wavelengths.

Two particular emission systems have been revealed, according to the pitch of the grating. For a pitch of 3 µm, the dispersion relation is asymptotic in the free propagation zone. The coupling can then be carried out only towards a restricted set of wavelengths but for a substantial range of wave vectors. The emission obtained with such a pitch of 3 µm is monochromatic and isotropic. For a pitch of 6.25 µm, the dispersion relation connects each wavelength of free propagation to a specific wave vector. The light emission is carried out in this case according to a broad spectrum, with each wavelength being emitted according to a precise angular direction.

The directional aspect of the emission is associated with the presence of a certain degree of spatial coherency of the emission of light. A spatial coherency length is as such estimated to a magnitude of a few hundred microns.

In the case of a layer of SiC, the coupling phenomenon is limited to a spectral range between 10 µm and 13 µm, a range for which the material has a non-zero complex index. In order to extend the application to the field of detecting $CO_2$, the layer of material can be made of tungsten which can be heated to a temperature of more than 2000 K, as described in the document of M. Laroche et al., "Highly directional radiation generated by a tungsten thermal source", Optics Letters, Vol. 30, Issue 19, pp. 2623-2625 (2005). With a periodic grating having a pitch of 3 μm and an engraving depth of 150 nm, it is possible to then emit a directional beam at a wavelength of 4.25 μm with a beam angle of about 25°.

The document of I. Puscasu et al., "Photonic crystals enable infrared gas sensors", Nanoengineering: Fabrication, Properties, Optics, and Devices. Edited by Dobisz, Elizabeth A.; Eldada, Louay A. Proceedings of the SPIE, Volume 5515, pp. 58-66 (2004), describes similar phenomena obtained by the interaction of plasmons (surface modes on metal interfaces) in structures of the photonic crystal type. The light source here comprises a metal layer that comprises a structuring made in 2 dimensions in the form of a matrix of holes a few microns deep. The metal layer is arranged on a semiconductor membrane (silicon). The grating of holes passes through the metal layer and also structures the semiconductor membrane. The presence of this structure described as a photonic crystal has for effect to reinforce the emission in a narrow band of wavelengths corresponding to the spectral absorption band of $CO_2$. The spectral position of the emission bandwidth can be tuned by the pitch of the grating of holes. However, with such a device, the energy lost outside of this band is not transferred in the emission bandwidth: the level of the energy peak remains less than that of the black body brought to the same temperature.

DESCRIPTION OF THE INVENTION

Thus there is a need to propose a new type of light-emitting device that makes it possible to control the spectral emission bandwidth, the angular direction of emission as well as the form of the light radiation emitted by the device.

For this, one embodiment proposes a light-emitting device comprising at least:
a metal layer able to be heated and to propagate surface waves consecutive to the heating of the metal layer, the metal layer being structured such that it comprises several diffraction patterns able to carry out a diffraction of the surface waves to free-space propagation modes, and wherein a synthetic hologram is encoded, or coded, such that a phase image of each pixel of the hologram is encoded, or coded, by an offset in the position of one of the diffraction patterns;
means able to heat the metal layer, or a heater of the metal layer.

Another embodiment proposes a light-emitting device comprising at least:
a metal layer able to be heated and to propagate surface waves consecutive to the heating of the metal layer, the metal layer being structured such that it comprises several diffraction patterns able to carry out a diffraction of the surface waves to free-space propagation modes, and wherein a synthetic hologram able to control the form of a light radiation intended to be emitted by the light-emitting device via controlling the wavefront intended to be emitted is coded such that the synthetic hologram corresponds to a phase image coded in each pixel by an offset of the position of one of the diffraction patterns in relation to a reference position of said one of the diffraction patterns;
a heater of the metal layer.

Such a light-emitting device therefore makes it possible to optimise its light emission by introducing therein, via the diffraction patterns, a periodic perturbation that generates a coupling between guided modes confined on the surface of the metal layer (surface waves) and free-space propagation modes. In addition, such a light-emitting device also comprises a synthetic hologram that modifies the phase of the diffracted wave thanks to a calculated distribution of the diffraction patterns for each pixel, with this synthetic hologram making it possible in particular to control the form of the light radiation emitted by the device via controlling the wavefront emitted.

The adaptation of the wavefront carried out by the synthetic hologram therefore makes it possible to obtain a distribution of intensity chosen in the image reconstruction plane, i.e. in the plane intended to receive the light emission from the device. This plane responds to the criterion of the Fourier optic for reading the synthetic hologram, or Fourier transform hologram.

The layer of metal material may correspond here to a layer of polar material wherein the synthetic hologram is encoded.

The phase image of each pixel of the synthetic hologram may be coded, or encoded, by an offset, along a first axis, of a position of said one of the diffraction patterns in relation to a reference position of said one of the diffraction patterns, wherein the reference positions of the diffraction patterns may be defined as corresponding to intersections of a grid of n lines and of m columns that may be regularly spaced from each other, the first axis being parallel to the n lines or to the m columns of the grid, wherein the diffraction patterns may be regularly spaced from each other along a second axis perpendicular to the first axis, and wherein each offset of position of one of the diffraction patterns in relation to its reference position being less than a distance p that separates two adjacent lines or two adjacent columns of the grid, with n and m integers greater than 1.

In each pixel, the phase image may be coded, or encoded, by an offset, along a first axis, of a position of said one of the diffraction patterns in relation to the reference position of said one of the diffraction patterns, the reference positions of the diffraction patterns may be defined as corresponding to intersections of a grid of n lines and of m columns regularly spaced from each other, the first axis being parallel to the n lines or to the m columns of the grid, the diffraction patterns may be regularly spaced from each other along a second axis perpendicular to the first axis, and each offset in position of one of the diffraction patterns in relation to its reference position may be less than a distance p that separates the two adjacent lines or two adjacent columns of the grid, with n and m integers greater than 1.

Each diffraction pattern is in this case offset from its nominal position by a value that corresponds to the phase offset desired on the wavefront to be generated by the device. The offsets in position of at least some of the diffraction patterns are in this case not zero.

In this case, the diffraction patterns may have dimensions that are substantially similar to each another, and/or a relationship between a dimension of each diffraction pattern according to the second axis and a dimension of said each diffraction pattern according to the first axis may be greater than or equal to approximately 1.5, and/or a surface of a section of each diffraction pattern, in a main plane of the metal layer, may be greater than or equal to about $p^2/2$ or wherein the diffraction patterns may comprise openings made through at least a part of the thickness of the metal layer and a surface of a section of each diffraction pattern, in a main plane of the metal layer, may be greater than or equal to about $p^2/2$.

According to an alternative, each diffraction pattern may form a part of a diffraction grating comprising several slots parallel to each other, with the phase image of each pixel of the synthetic hologram being encoded by an offset, along a first axis, of a position of the parts of the slots of said one of the diffraction patterns in relation to a reference position of said one of the diffraction patterns, with the reference positions of the diffraction patterns being defined as corresponding to the positions wherein the parts of the slots of all of the diffraction patterns are aligned in relation to each other. The offsets in position of the diffraction patterns correspond in this case to phase offsets of the diffraction grating introduced individually for each pixel of the synthetic hologram.

Each diffraction pattern may form a part of a diffraction grating that comprises several slots parallel to one another, wherein, in each pixel, the phase image may be encoded by an offset, along a first axis, of a position of the parts of the slots of said one of the diffraction patterns in relation to the reference position of said one of the diffraction patterns, and wherein the reference positions of the diffraction patterns may be defined as corresponding to the positions wherein the parts of the slots of all of the diffraction patterns are aligned in relation to each other.

The shifts in position of at least some of the diffraction patterns are in this case not zero.

The diffraction patterns may comprise openings made through at least a part of the thickness of the metal layer.

Each of the openings may be of a substantially elliptic shape or each of the openings may correspond to a line segment.

The metal layer may comprise a thickness greater than about 200 nm, and the openings may be made in a part of the metal layer with a depth between about 50 nm and 200 nm.

The means able to heat the metal layer, or the heater of the metal layer, may comprise at least one electrically conductive element coupled thermally with the metal layer and able to be heated when an electric current passes through it.

The electrically conductive element may comprise a stack of the TiN/Pt/TiN type, and/or the metal layer may comprise tungsten and/or platinum. The metal of the metal layer may be chosen according to the range of wavelengths intended to be diffracted and emitted in the form of a hologram by the device. As such, a metal layer comprising SiC can be adapted for an emission in a band of wavelengths between about 10.5 μm and 12.5 μm. A metal layer comprising tungsten and/or platinum has however for advantage, compared to SiC, to allow for an emission in a wider range of wavelengths, and in particular in a range that includes the absorption peak of $CO_2$.

The light-emitting device may further comprise a mechanical support element whereon is arranged the metal layer and/or, when the means able to heat the metal layer, or the heater of the metal layer, comprise the electrically conductive element, an electric isolation element arranged between the electrically conductive element and the metal layer.

The means able to heat the metal layer, or the heater of the metal layer, may comprise at least one device able to circulate an electric current through the metal layer or, when said means or heater comprise the electrically conductive element, a device able to circulate an electric current through the electrically conductive element.

The light-emitting device may further comprise at least one Fourier lens arranged at a front focal distance, or front focal length, from the metal layer and at a rear focal distance, or rear focal length, from a plane intended to receive the light emission from the device. Such a Fourier lens makes it possible to reconstruct the image of the hologram on the plane intended to receive the light emission from the device.

Alternatively, a phase function of the synthetic hologram encoded in the metal layer may comprise an optic function that is substantially similar to a convergence function of a Fourier lens.

As such, the reconstruction of the image of the hologram is obtained in its plane of reconstruction without calling upon a Fourier lens, which makes it possible to carry out a direct reading of the wavefront emitted.

A phase function of the synthetic hologram encoded in the metal layer may comprise an optic function, for example of the cylindrical lens type, able to compensate for a deformation of the light-emitting device during the heating of the metal layer. As such, a deformation due to the heating of the metal layer can be compensated by taking this deformation into account during the encoding of the synthetic hologram, and by integrating for example an inverse deformation, of the cylindrical lens type, in the hologram which offsets that undergone by the light-emitting device.

An image of the synthetic hologram may be a slot. Generally, the image of the synthetic hologram is chosen according to the form of the light radiation desired, and therefore of the application considered for the light-emitting device. An image corresponding to a slot is well adapted when the light-emitting device is intended to be part of a gas sensor.

Another embodiment concerns a gas sensor comprising at least one light-emitting device as described above, and one detector able to detect the presence of at least one gas in a space through which at least one image of the hologram emitted by the light-emitting device passes through. Compared to gas sensors of prior art, such a gas sensor requires less elements, and in particular less optic elements for formatting, or shaping, the light radiation emitted by the incandescent light source.

The image coded in the hologram may in particular be adapted to the geometry of the detector of the gas sensor.

The detector may be able to carry out a spectral detection of the image of the hologram at least in a range of wavelengths that comprises at least one spectral absorption band of the gas or gases intended to be detected by the sensor.

In this case, the detector may be able to carry out a spectral detection of several images of the hologram emitted by the light-emitting device in several ranges of wavelengths of which at least one comprises the spectral absorption band of the gas or gases intended to be detected by the sensor.

Alternatively, the detector may be able to carry out a spectral detection of a single image of the hologram emitted by the light-emitting device in a single range of wavelengths that comprises the spectral absorption band of the gas intended to be detected by the sensor.

In another alternative, the detector may comprise at least:
  a reflective element arranged facing the light-emitting device and able to reflect the image of the hologram that has passed through the space comprising the gas or gases towards the light-emitting device;
  a device for measuring the electrical resistance of the metal layer or, when the means able to heat the metal layer or the heater of the metal layer comprise the electrically conductive element, a device for measuring the electrical resistance of the electrically conductive element.

In this case, only the reflecting element, and not the entire detecting structure, is intended to be located in the plane of reconstruction of the image of the hologram, which simplifies the making of the sensor. The detection may in this case be obtained by measuring the variation in the value of the electrical resistance of the light source, therefore of the metal layer or of the electrically conductive element of the light-emitting device.

Another embodiment concerns a photovoltaic device that comprises at least one light-emitting device as described above, wherein the metal layer of the light-emitting device is able to receive light rays received by the photovoltaic device, and further comprising at least one photovoltaic conversion element able to receive an image of the hologram intended to be emitted by the light-emitting device. As such, the light-emitting device, which is able to absorb the broad solar spectrum received by the photovoltaic device, makes it possible to re-emit the solar energy received to the photovoltaic conversion element in a spectral range adapted to this element, and as such increase the conversion efficiency of the element in relation to a photovoltaic device comprising the same photovoltaic conversion element but not comprising the light-emitting device as described above.

Another embodiment concerns a photovoltaic device comprising at least one light-emitting device, wherein the light-emitting device comprises at least:
 a metal layer able to be heated and to propagate surface waves consecutive to the heating of the metal layer, the metal layer being structured such that it comprises several diffraction patterns able to carry out a diffraction of the surface waves to free-space propagation modes, and wherein a synthetic hologram able to control the form of a light radiation intended to be emitted by the light-emitting device via controlling the wavefront intended to be emitted is coded such that the synthetic hologram corresponds to a phase image coded in each pixel by an offset of the position of one of the diffraction patterns in relation to a reference position of said one of the diffraction patterns;
 and wherein the metal layer of the light-emitting device is able to receive light rays received by the photovoltaic device, and further comprising at least one photovoltaic conversion element able to receive an image of the hologram intended to be emitted by the light-emitting device.

BRIEF DESCRIPTION OF THE DRAWINGS

This invention shall be better understood when reading the description of embodiments provided solely for the purposes of information and in no way restrictive, in reference to the annexed drawings wherein.

Identical, similar or equivalent portions of these various figures described hereinafter bear the same numerical references so as to facilitate the passing from one figure to the other.

The different portions shown in the figures are not necessarily shown according to a uniform scale, in order to make the figures more legible.

The different possibilities (alternatives and embodiments) must be understood as not being exclusive from one another and can be combined together.

DETAILED DESCRIPTION OF PARTICULAR EMBODIMENTS

Figure 1:
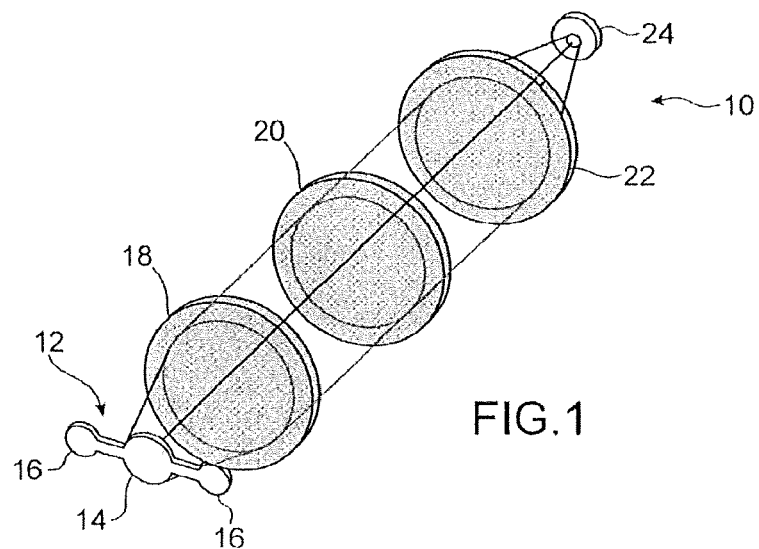
FIG. 1 diagrammatically shows a gas sensor according to prior art.
Figure 2:
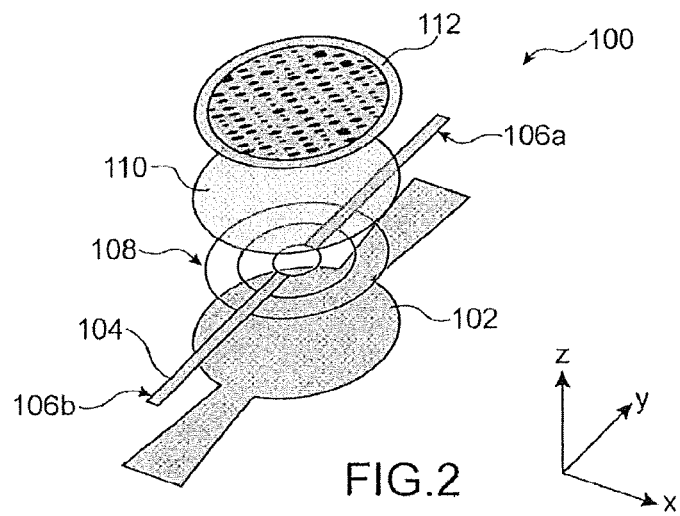
FIGS. 2 and 3 diagrammatically show a light-emitting device according to a particular embodiment.
Figure 3:
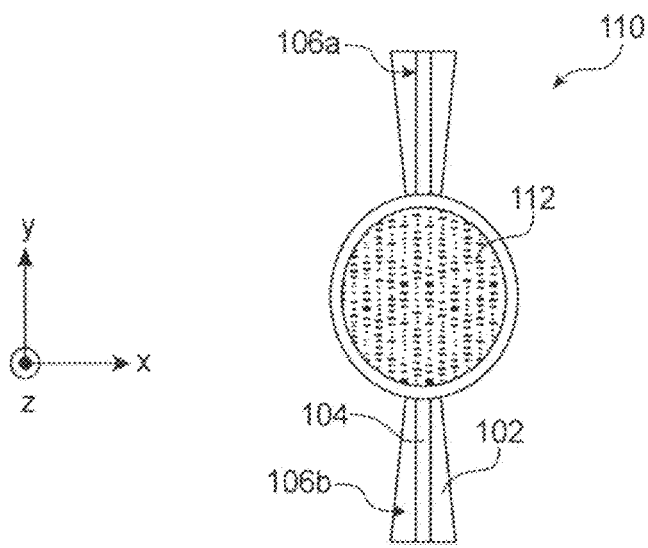

A light-emitting device 100 according to a particular embodiment is diagrammatically shown in FIGS. 2 and 3 (as an exploded view in 3 dimensions in FIG. 2 and as a top view in FIG. 3).

The light-emitting device 100 comprises a mechanical support element 102 for example $Si_3N_4$-based. An electrically conductive element 104, corresponding for example to a TiN/Pt/TiN stack, is arranged on the mechanical support element 102. The electrically conductive element 104 is able to be heated when an electric current passes through it. Two longitudinal portions 106a and 106b of the electrically conductive element 104 (which rest on two longitudinal portions of the mechanical support element 102) form two electrical connection pads of the electrically conductive element 104, and therefore of the device 100.

The electrically conductive element 104 also comprises a central portion 108, formed of several portions of electrically conductive material in the form of concentric rings and electrically connected to the two longitudinal portions 106a, 106b. This central portion 108 of the electrically conductive element 104 (which rests on a central portion in the form of a disc of the mechanical support element 102) is intended to manage the heating. The device 100 also comprises an electric isolation element 110, here in the form of a disc, comprising $SiO_2$ and which covers the central portion 108 of the electrically conductive element 104.

The light-emitting device 100 further comprises a complementary thermal diffusion element corresponding to a metal layer 112, here in the form of a disc, arranged facing the central portion 108 of the electrically conductive element 104 and comprising for example tungsten and/or platinum, structured by a grating of openings (i.e. of hollows or holes) that form diffraction elements, or diffraction patterns. In addition, this grating of openings formed in the layer 112 is also made such that it encodes within it a synthetic hologram. The patterns of the structuring made in the layer 112 can be made, for example by engraving, through the entire thickness of the layer 112 or only a part of the thickness of the layer 112, with this part being for example between about 50 nm and 200 nm.

The metal layer 112 is electrically isolated from the electrically conductive element 104 thanks to the electric isolation element 110 arranged between the metal layer 112 and the electrically conductive element 104. However, the metal layer 112 is thermally coupled with the central portion 108 of the electrically conductive element 104. As such, the heating of the central portion 108 of the electrically conductive element 104 produced by the passing of the current through the latter is transmitted to the metal layer 112. The heating of the metal layer 112 then produces waves that propagate at the surface of the metal layer 112. These surface waves are diffracted by the diffraction patterns made in the metal layer 112 to free propagation modes, with the light emission obtained which is carried out according to the synthetic hologram coded in the metal layer 112.

Figure 4:
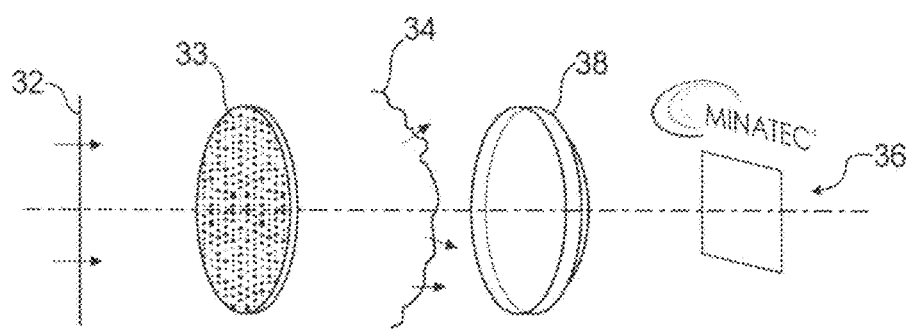
FIG. 4 shows the principle of the synthetic hologram encoded in the light-emitting device.

The principle of a synthetic hologram such as the one encoded in the layer 112 is diagrammatically shown in FIG. 4. A wavefront 32 arriving incidentally on a layer 33 wherein the synthetic hologram is encoded is modified by the structurings of the layer 33 (corresponding to the diffraction patterns in the case at hand), generating a modified wavefront 34 that carries the information relative to the hologram encoded. The desired image 36 is obtained through reconstruction by having the modified wavefront 34 pass through a Fourier lens 38 carrying out an inverse Fourier transform of the modified wavefront 34.

The image and the modified wavefront are connected by a Fourier transform. The design of the hologram corresponds to defining a structure that makes it possible to generate the modified wavefront 34. For this, this structure must be able to modify the phase of the incident wave in a controlled manner. Such a structure may correspond to a diffraction structure manufactured in a metal layer (amplitude hologram).

In the light-emitting device 100, the metal layer 112 is not passed through by a wavefront arriving incidentally on the latter. Indeed, in the light-emitting device 100, it is the heating of the metal layer 112 that causes the generation of surface waves which are then diffracted by the diffraction patterns to free-space propagation modes, as such generating the light emission of a wavefront similar to wavefront 34, transporting the information relative to the hologram encoded.

Figure 5:
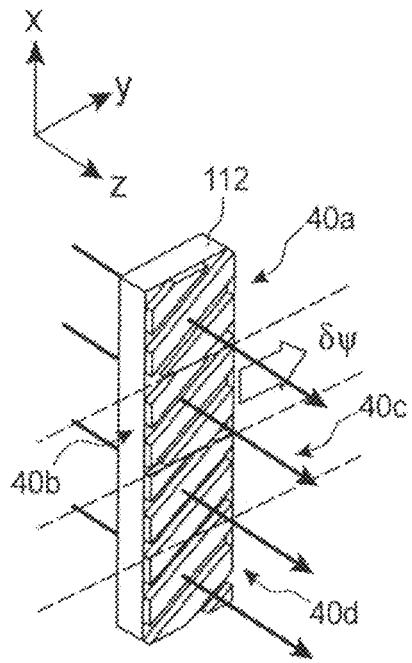
FIGS. 5 and 6 show examples of diffraction patterns carried out in a metal layer of a light-emitting device.

A first embodiment of the diffraction patterns made in the metal layer 112 is shown in FIG. 5. The metal layer 112 is structured according to a pattern that forms a diffraction grating. The modification of the phase of the waves generated at the surface of the metal layer 112 is obtained by modifying the phase of the diffraction grating at each pixel of the image of the hologram, i.e. at each diffraction pattern. In the example of FIG. 5, four parts of the metal layer 112 correspond to four pixels of the hologram and form four diffraction patterns 40a-40d. The diffraction grating formed by the diffraction patterns corresponding to the pixels of the hologram is formed by a grating of slots oriented parallel to one another. Each diffraction pattern is therefore formed by a part of these slots located on each part of the metal layer 112 associated with the pixel. In FIG. 5, the slots are oriented according to a direction included in the plane (X, Y). For each pixel, the phase offset carried out corresponds to an offset of the corresponding part of slots along the Y axis in relation to a reference position. The reference positions of the diffraction patterns correspond to the positions wherein the parts of slots of all of the diffraction patterns are aligned in relation to one another. The diffraction grating shows the binary image of the interferences between the surface waves generated by the heating of the metal layer 112 and the wavefront emitted by the metal layer 112 corresponding to the hologram. When the hologram is reconstructed, the wavefront emitted by the metal layer 112 is recovered according to the diffraction orders of the grating, with order 0 not comprising any modification of its phase. The document "Binary computer-generated holograms" of Wai-Hon Lee, Applied Optics, vol. 18, no. 21, Nov. 1, 1979, describes for example the making of such a synthetic hologram.

Figure 6:
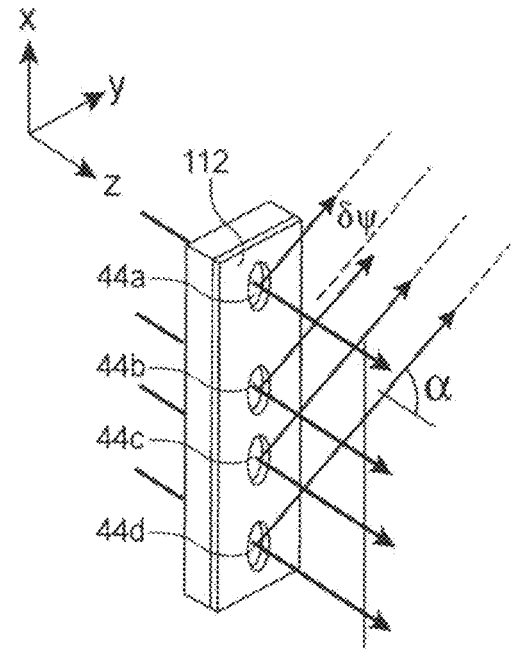

A second embodiment of the diffraction patterns made in the metal layer 112 is shown in FIG. 6. The metal layer 112 is structured according to a meshing of diffraction patterns. In FIG. 6, four diffraction patterns 44a-44d, make it possible to carry out the diffraction of the surface waves on four pixels are shown and each have, in the plane (X, Y) of the metal layer 112, an oval-shaped section. The introduction of offsets in the distribution of the patterns according to one of the axes of the plane of the metal layer 112 (the axis X in the example of FIG. 6), in each part of the metal layer 112 corresponding to a pixel, corresponds to locally introducing phase shifts on the waves generated according to certain diffraction orders of the grating. A hologram obtained with such a diffraction structure is called a detour-phase hologram and is for example described in the document of A. W. Lohmann and D. P. Paris (1967), "Binary Fraunhofer Holograms, Generated by Computer," Appl. Opt. 6, 1739-1748. Such a diffraction structure is simpler to make than that described in relation with FIG. 5 since it is comprised of the repeating of a pattern with a size in the vicinity of the pitch of the diffraction structure and not of the repetition of lines with a width that is much less than the pitch of the diffraction structure.

Figure 7:
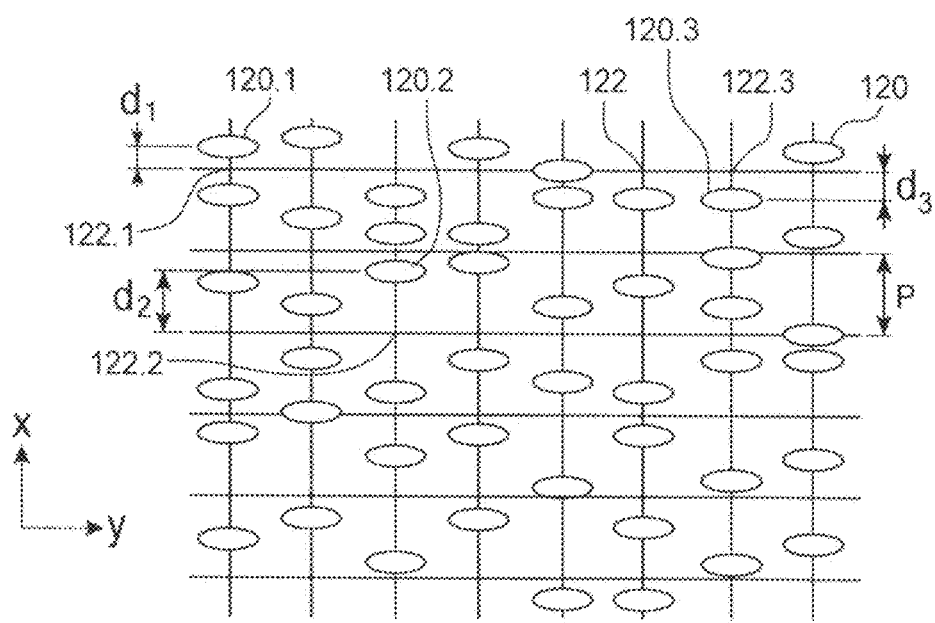
FIG. 7 shows an example of arrangements of diffraction patterns in relation to their reference position, with these patterns encoding a synthetic hologram.

As such, in the metal layer 112, a synthetic hologram is encoded such that a phase image of each pixel of the hologram is encoded by an offset, along a first axis, of a position of one of the diffraction patterns in relation to a reference position of this diffraction pattern. FIG. 7 diagrammatically shows an example of the arrangement of the diffraction patterns in a part of the layer 112 when the diffraction patterns are made by openings such as described hereinabove in relation with FIG. 6. In this embodiment, the diffraction patterns correspond to openings 120 made through a part of the thickness of the layer 112. The reference positions 122, or nominal positions, of the diffraction patterns 120 are defined as corresponding to intersections of a grid of n lines and of m columns that are regularly spaced from each other. The numbers n and m are integers of which the values correspond to the number of lines and columns of pixels of the hologram. The first axis is here parallel to the m columns of the grid. The diffraction patterns are regularly spaced from each other along a second axis (axis Y) perpendicular to the first axis, and each offset in the position of one of the diffraction patterns in relation to the reference position is less than a distance p separating two adjacent lines or two adjacent columns of the grid. Several examples of offsets d1, d2 and d3 of diffraction patterns 120.1, 120.2 and 120.3 in relation to their reference position 122.1, 122.2 and 122.3 are shown in FIG. 7.

Note that the encoding of the hologram may result in a zero offset for some diffraction patterns in relation to their reference position.

Figure 8:
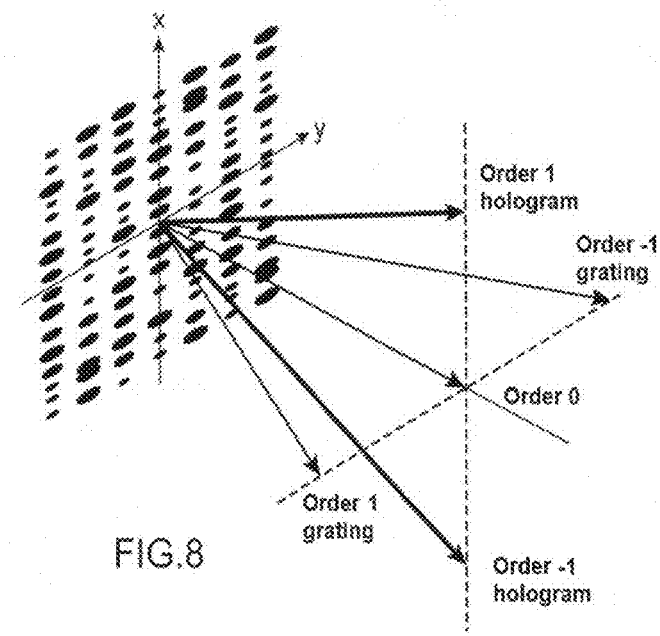
FIG. 8 shows a diagram for reading a synthetic hologram.

FIG. 8 shows a diagram for reading a detour-phase hologram, similar to the one encoded in the metal layer 112 and such as described hereinabove in relation with FIGS. 6 and 7. Only the diffraction according to the axis of modification of the position of the patterns (axis X in the example described here) makes it possible to generate the wavefront emitted from the metal layer 112. This wavefront is found according to the positive and negative conjugated diffraction orders of the hologram, and primarily following the conjugated orders 1 and −1 of the hologram.

The method for reconstructing the image from the wavefront emitted may be of two types.

Figure 9:
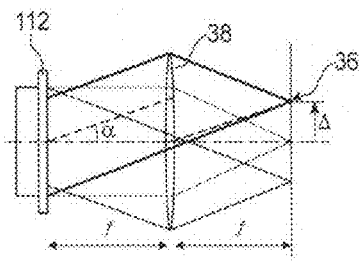
FIGS. 9 and 10 show methods of reconstructing an image of a hologram using a modified wavefront.

In a first case shown diagrammatically in FIG. 9, the Fourier lens 38 is positioned at a front focal distance from the metal layer 112 wherein the hologram is encoded. The image 36 is reconstructed in a plane of reconstruction located at a rear focal distance from the lens 38. The size of the image and its offset in relation to the optic axis are given by a parameter Δ calculated using the pitch of the diffraction patterns grating Λ, the wavelength λ and the focal f of the lens 38 such that:

$$\Delta = \frac{\lambda f}{\Lambda} \quad (1)$$

Figure 10:
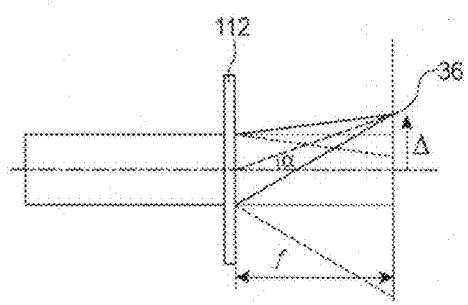

In a second case shown in FIG. 10, the convergence function may be introduced into the phase function of the hologram, with the patterns of the structuring of the metal layer 112 being made such that the metal layer 112 carries out this convergence function. The phase of the hologram Δϕ(r) is radially modified according to the focal value desired such that:

$$\Delta\varphi(r) = \frac{\pi \times r^2}{\lambda f} \quad (2)$$

The encoding of the phase function of the Fourier lens in the metal layer 112 is limited by the size of the hologram cell. A limit may be defined when the phase variation of the Fourier lens on a scale of a cell of the hologram exceeds 2π. A limit radius $R_{lim}$, and a limit focal $f_{lim}$, are deduced from this, such that:

$$R_{lim} = \frac{\lambda f + \Lambda^2}{2\Lambda} \approx \frac{\lambda f}{2\Lambda} \quad (3)$$

$$f_{lim} = \frac{2\Lambda \times R_{max} - \Lambda^2}{\lambda} \approx 2\frac{\Lambda \times R_{max}}{\lambda} \quad (4)$$

By way of example, at a wavelength λ of 4.25 μm and for a hologram pitch Λ of 5 μm the limit focal $f_{lim}$ for a radius R of 250 μm is 0.6 mm.

The second case disclosed hereinabove differs from the first case because the image can be seen only in the first order of the hologram, the conjugated order −1 represents an inverted focal lens function, or a divergent beam.

The pitch of the diffraction patterns grating Λ, or pitch of the hologram, corresponds to the distance that separates two reference positions of two adjacent diffraction patterns made in the metal layer 112.

As the hologram is encoded in the metal layer 112, the light-emitting device 100 forms an "emitting hologram". Each diffraction pattern made in the metal layer 112 therefore forms a punctual light source that is not connected to a wave external to the device 100. The emission of these different sources is correlated via a spatial coherency effect due to the propagation of the surface waves in the metal layer 112 generated by the heating of this layer caused by the passing of current in the electrically conductive element 104.

As in the emitting devices that comprise a periodic grating or a structure of the photonic crystal type, the generation of a surface wave in the metal layer 112 is disturbed by the presence of the periodic structuring made on this same surface. Because the parameters of the periodic structuring of the metal layer 112 are adapted to the dispersion relation of the surface modes, a coupling of these modes towards free-space propagating waves is possible. In addition, in accordance with the principle of detour-phase holograms, due to the fact that the periodic distribution of the coupling structure is modified, the wavefront of the propagating wave is also modified. As such, in the emitting device 100, the generation of a controlled wavefront is obtained using an incandescence phenomenon. As such, the device 100 emits a light beam in a range of wavelengths and according to a beam angle α determined via the pitch of the diffraction patterns grating formed in the metal layer 112, the light beam emitted by the device 100 being furthermore distributed according to an image of which the form and the positioning correspond to the hologram encoded in this diffraction patterns grating formed in the metal layer 112.

Figure 11:
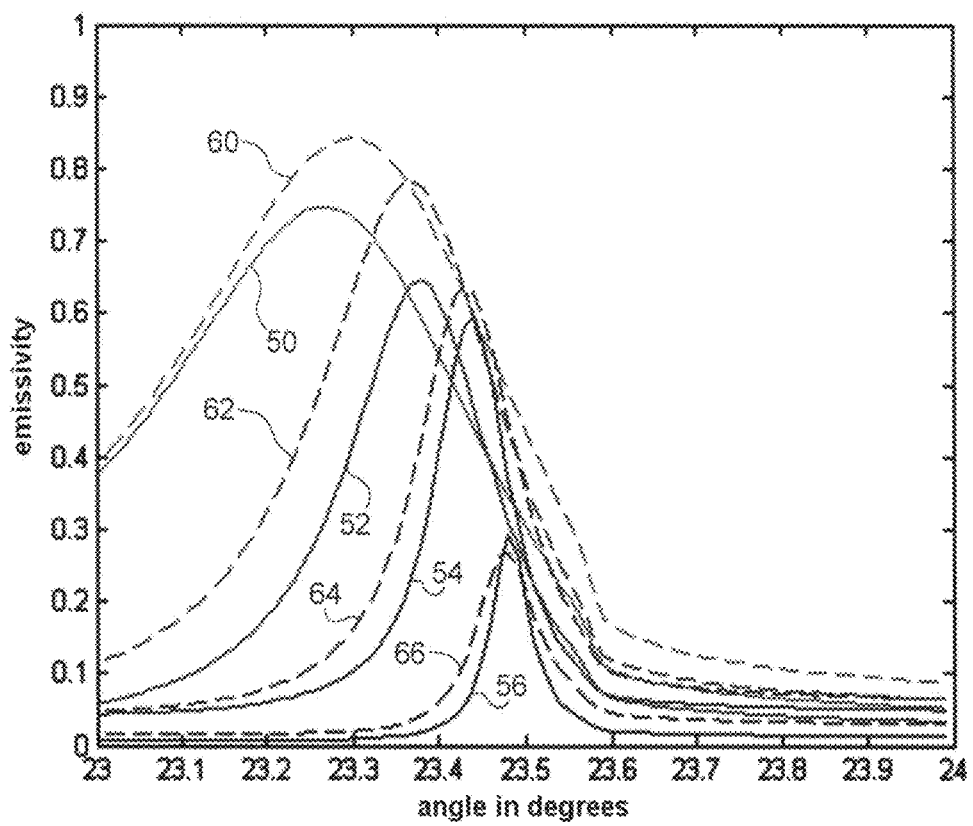
FIG. 11 shows curves of angular emissivity obtained for different materials and different diffraction patterns formed in the light-emitting device.

The curves of FIG. 11 show the angular emissivity of the metal layer 112, i.e. the level of emissivity obtained according to the angle, wherein a synthetic hologram is encoded by openings such as those described hereinabove in relation with FIGS. 6-8, for different depths of openings forming the diffraction patterns and for different materials. For all of these curves, the emissivity is measured for a wavelength of 4.2 μm and for a grating pitch (distance between the reference positions of two adjacent diffraction patterns) equal to 3 μm. The curves 50, 52, 54 and 56 correspond to the emissivity obtained with a metal layer 112 made of tungsten, with openings made respectively at depths of 50 nm, 100 nm, 150 nm and 200 nm. The curves 60, 62, 64 and 66 correspond to the emissivity obtained with a metal layer 112 made of platinum, with openings made respectively at depths of 50 nm, 100 nm, 150 nm and 200 nm. It can be seen on these curves that an optimum is obtained with openings made with a depth located between about 100 nm and 150 nm.

Advantageously, the hologram is calculated by a method of scrambling the phase, as for example described in the document "Use of a random phase mask for the recording of Fourier transform holograms of data masks" of C. B. Burckhardt, Appl. Opt. 9(3), 695-700 (1970), and the amplitude of the hologram is set in such a way that the filling rate of the cells of the hologram, corresponding to the ratio of the surface of the diffraction pattern over the surface of the part of the metal layer 112 corresponding to one pixel is equal to at least 50%. In addition, the ratio between the size of the patterns of the structuring of the metal layer 112 in the direction perpendicular to the phase encoding (axis Y in the example of FIG. 7) and the size in the direction of the phase encoding (axis X in the example of FIG. 7) is preferably at least equal to 1.5. The diffraction patterns also preferably have dimensions that are substantially similar in relation to one another.

The image of the hologram encoded in the metal layer 112 can be reconstructed by optically coupling the light-emitting device with a Fourier lens according to the principle described hereinabove in relation with FIG. 9. Alternatively, a phase function of the synthetic hologram encoded in the metal layer 112 may comprise an optic function substantially similar to a convergence function of a Fourier lens, in accordance with the principle described hereinabove with FIG. 10.

It is also possible for a phase function of the synthetic hologram encoded in the metal layer 112 to comprise an optic function of the cylindrical lens type able to compensate for a deformation of the light-emitting device 100, due to a deformation of the metal layer 112 (and possibly of the electrically conductive element 104 when the device 100 comprises such an element) during the heating of the metal layer 112. The synthetic hologram encoded makes it possible as such to compensate for a curvature effect linked to the presence of constraints on the layers of the light-emitting device 100. For this, knowing this curvature effect, the hologram is encoded with an inverse curvature effect which makes it possible, during the reconstruction of the image of the hologram, to obtain a cancellation of the curvature effect. This results in the introduction of a phase component of this cylindrical lens type given by an equation similar to the equation (3) hereinabove.

For example, the light device 100 can undergo a convex deformation according to the axis x (axis shown in FIGS. 2 and 3) leading to a radius of curvature equal to 1 mm. In this case, the holographic emission is disturbed by a divergent lens effect having a focal equal to 1 mm. In order to correct this effect, it is possible to add a convergent phase correction to the phase function of the hologram such that $\Delta\phi(x)=\pi \cdot x^2/(\lambda \cdot f)$ with f=1 mm.

Given the diffraction patterns made in the metal layer 112, the coupling of the surface waves is carried out for a given pair of wavelength/beam angle parameters. The position of the holographic image in the plane of reconstruction similarly depends on the wavelength as indicated in the equation (1).

Figure 12:
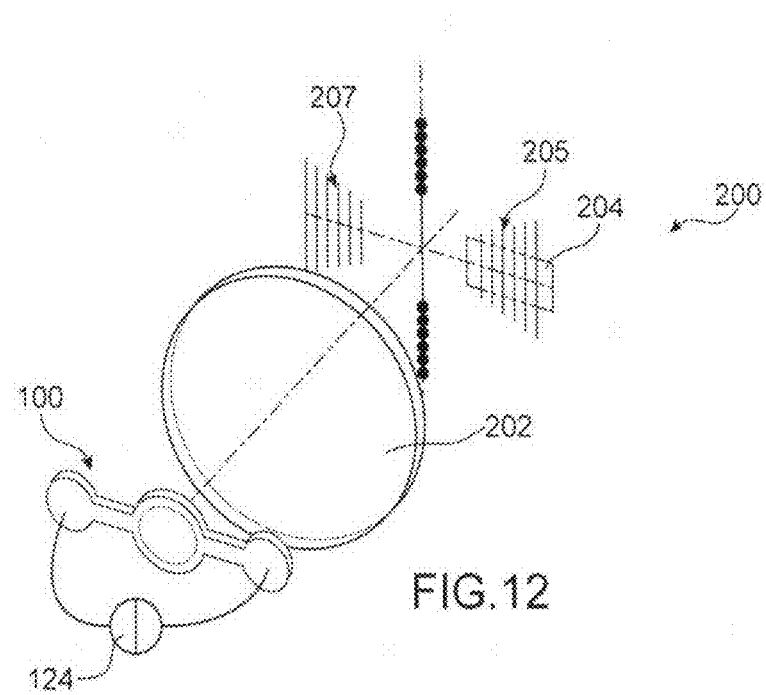
FIGS. 12 to 16 show a gas sensor according to several embodiments.

A first embodiment of a gas sensor 200 is described in relation with FIG. 12. The gas sensor 200 comprises the light-emitting device 100 similar to the one described hereinabove in relation with FIG. 2. The light-emitting device 100 comprises a Fourier lens 202 arranged at a front focal distance from the metal layer 112 of the device 100. The gas sensor 200 also comprises a matrix detector 204 (comprising several photodetectors arranged in a matrix) arranged in the plane of reconstruction of the hologram, at a rear focal distance from the Fourier lens 202. The device 100 further comprises a current generator 124 connected to the electrical connection pads of the electrically conductive element 104 in order to circulate a current through the electrically conductive element 104 and as such cause a heating of the metal layer 112. When the device 100 does not have the electrically conductive element 104, the current generator 124 may be connected directly to the metal layer 112 so that the latter is traversed by the current generated by the generator 124.

In this first embodiment, the hologram image encoded in the metal layer 112 of the device 100 corresponds to a slot. As such, the reconstructing of the hologram in the plane of reconstruction gives the image of several slots 205 of different wavelengths arranged next to one another and spaced laterally from one another. The detector 204 is arranged in the zone where the diffraction order 1 of the hologram is located. Slots 207 are also present in the zone where the diffraction order −1, or conjugated, of the hologram is located.

The gas sensor 200 is intended to carry out a detection of the presence of $CO_2$. The light emitted by the emitting device 100 passes through a space (between the device 100 and the plane of reconstruction of the hologram where is arranged the detector 204) wherein the gas to be analysed is located. Given the absorption peak generated by the presence of $CO_2$ in the light spectrum (absorption peak at about 4.25 μm), the detector 204 can as such easily detect this peak at the image of the slot of which the spectral band includes this wavelength due to the fact that this results in a slot of lower intensity than that of the other slots. In such a sensor, the emissive source part and the spectral dispersion part are integrated into the emitting device 100. In addition, the optic part of the sensor corresponds to only a single Fourier lens, which reduces the bulk of the sensor 200 in relation to sensors of prior art calling upon several optics for formatting the light radiation.

Figure 13:
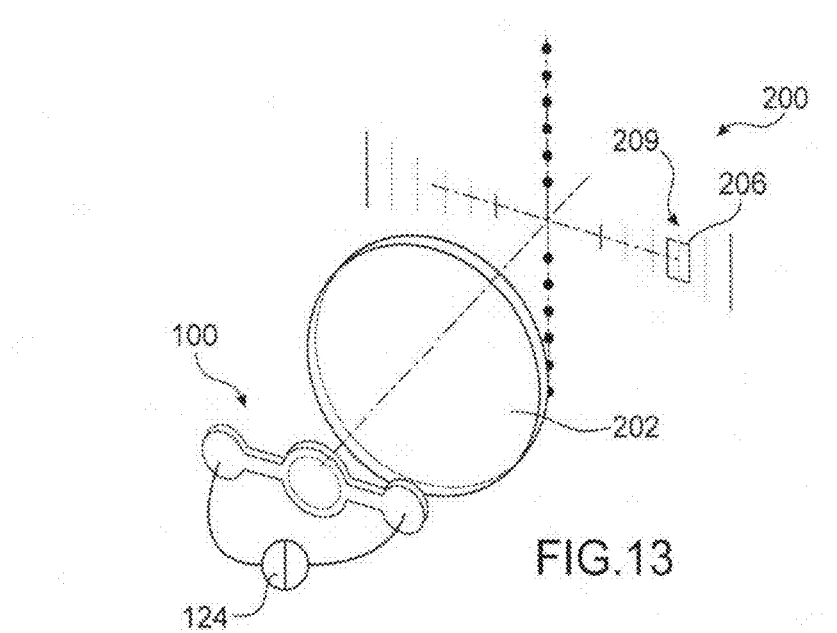

A second embodiment of the sensor 200 is shown in FIG. 13. Compared to the gas sensor 200 described hereinabove in relation with FIG. 12, the parameters of the Fourier lens 202 and of the hologram are modified in order to allow for a lateral wider distribution of the spectrum, i.e. slots that are further spaced from each other. In addition, a single photodetector 206 is positioned in the plane of reconstruction of the hologram in such a way as to select the only spectral band of interest, i.e. the slot 209 corresponding to the spectral absorption zone of the gaseous species to be measured, here $CO_2$.

Figure 14:
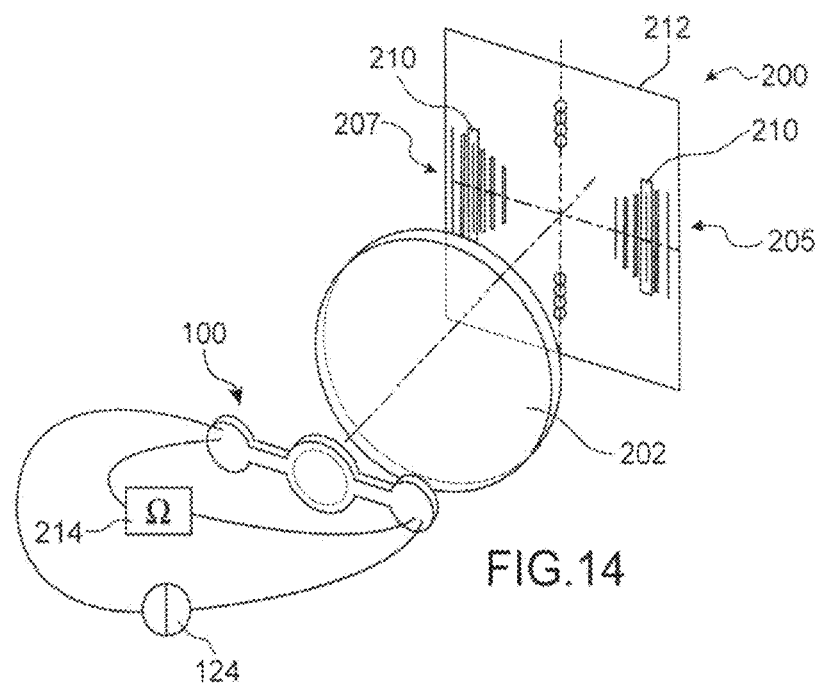

A third embodiment of the sensor 200 is shown in FIG. 14. In this embodiment, the detector comprises reflective strips 210 positioned on an absorbent background 212, on either side of the optic axis, i.e. in the zones where the diffraction orders 1 and −1 of the hologram are located.

Each of these strips 210 reflects a part of the spectrum dispersed by the hologram. The signal reflected is incident, in return, on the emitting device 100, and is coupled by the surface mode in the electrically conductive element 104 or, when the device 100 does not comprise the electrically conductive element 104, directly in the metal layer 112. This coupling causes a slight increase in the temperature of the electrically conductive element 104 (or of the metal layer 112) which can be detected by the change in its electrical resistance (in the presence of the absorption peak due to the $CO_2$, this change in resistance will not be as substantial). A device for measuring 214 the electrical resistance of the electrically conductive element 104 (or directly of the metal layer 112) is therefore connected electrically to the two electrical connection pads of the electrically conductive element 104 (or of the metal layer 112). The incandescent source of the device 100 therefore also plays, in this embodiment, a part of the role of detector of the sensor 200.

Figure 15:
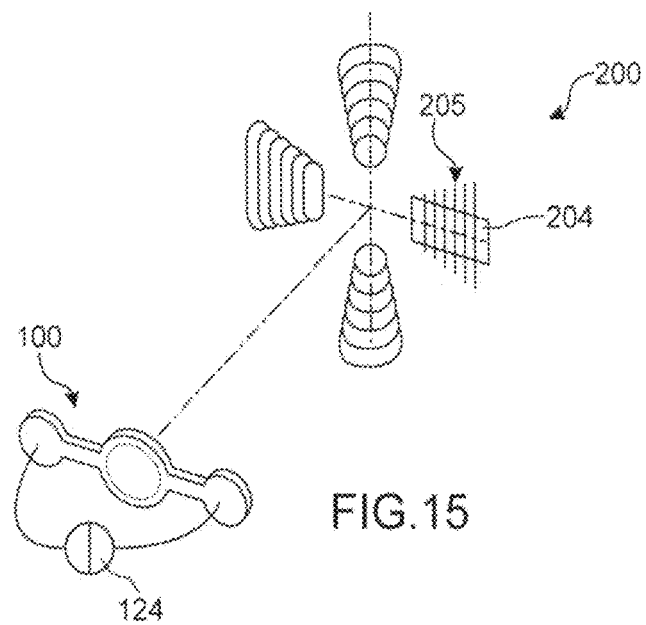

A fourth embodiment of the sensor 200 is shown in FIG. 15. Compared to sensor 200 described hereinabove in relation with FIG. 12, this sensor 200 does not comprise the Fourier lens 202. The hologram is directly reconstructed in the plane wherein the detector 204 is located due to the fact that a phase function of the synthetic hologram encoded in the metal layer 112 comprises an optic function that corresponds to a convergence function of a Fourier lens. The holographic image (slots 205) appears solely in the zone corresponding to the selected diffraction order, here order 1 of the hologram. A sensor of the matrix type 204 is positioned on the reconstructed image in order to detect the emission spectrum of the light source. Alternatively, the sensor of the matrix type 204 may be replaced with a photodetector 206 as for the sensor 200 described in relation with FIG. 13. In such a sensor, the emitting source part, the optic formatting part and the spectral dispersion part are integrated into the emitting device 100, which reduces the bulk of the sensor 200.

According to an embodiment, the metal layer 112 may correspond to a layer of tungsten of a thickness equal to about 250 nm and in the form of a disc with a diameter equal to about 250 μm. A hologram of a size equal to 80*80 pixels containing a square pattern of 5*5 pixels is encoded in the metal layer 112 with a pitch of approximately 3 μm and a depth of about 125 nm. A focal of 25 mm is added to the radial phase function. Given the absorption peak at about 4.25 μm, the slot is imaged at a longitudinal distance of 25 mm from the device 100 and at a lateral distance of 35 mm. The reproduced square holographic pattern has a size of about 2.2 mm in the plane of reconstruction. A detector of the PbSe type with a surface equal to approximately 2×2 mm² of the maximum sensitivity tuned to the wavelength 4.2

μm (corresponding for example to a detector of the P9696-202 type of the brand Hamamatsu®) is thus positioned at this location.

Figure 16:
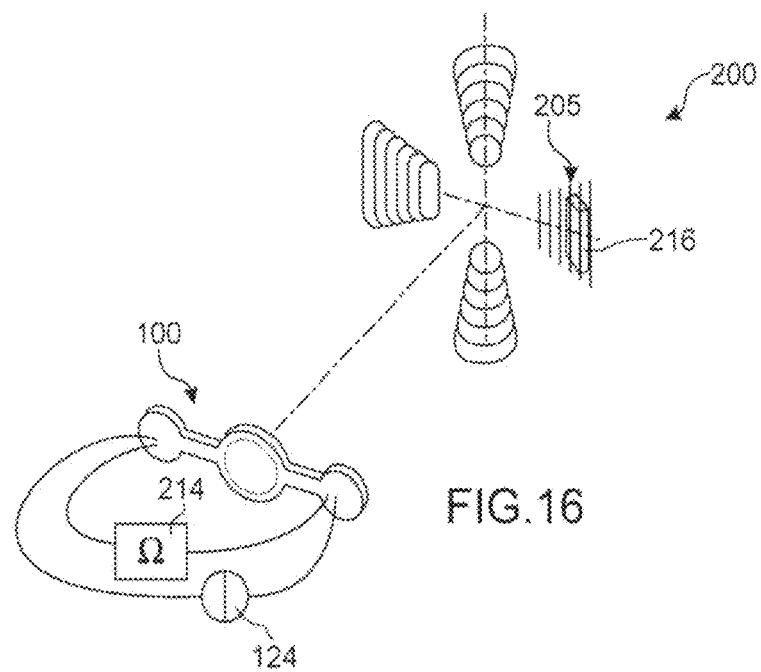

A fifth embodiment of the sensor 200 is shown in FIG. 16. As in the fourth embodiment described hereinabove, the emitting device 100 is made such that a phase function of the synthetic hologram encoded in the metal layer 112 comprises an optic function corresponding to a convergence function of a Fourier lens, as such allowing the sensor 200 to be made without a Fourier lens. In addition, in this fifth embodiment, only one reflective element 216 is arranged in the plane of reconstruction of the hologram, at the chosen diffraction order (order 1 in this example). This reflective element 216 is not oriented parallel to the plane of reconstruction, i.e. perpendicularly to the optic axis of the sensor 200, as in the case of reflective strips 210 of the sensor 200 described hereinabove in relation with FIG. 14.

The reflective element 216 is oriented in such a way as to turn the chosen spectral band in the direction of incidence, towards the emitting device 100. As in the third embodiment described hereinabove, a measuring device 214 of the electrical resistance of the electrically conductive element 104 (or of the metal layer 112) is connected electrically to the two electrical connection pads of the electrically conductive element 104 (or of the metal layer 112) in order to measure the presence of the gas to be detected via measuring the electrical resistance of the electrically conductive element 104 (or of the metal layer 112). In such a sensor, the emitting source part, the detection part, the optic formatting part and the spectral dispersion part are integrated into the emitting device 100, which substantially reduces the bulk of the sensor 200.

In the embodiments described hereinabove, the holographic image is a slot but other distributions that optimise the spectral detection intended to be carried out by the sensor may be used (for example a series of points).

Figure 17:
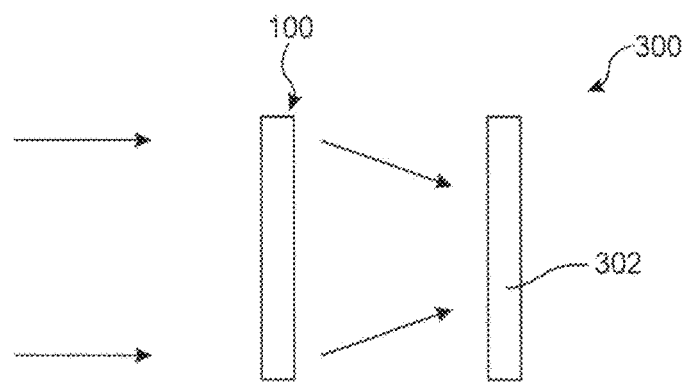
FIG. 17 shows a photovoltaic device according to a particular embodiment.

The light-emitting device 100 described hereinabove can advantageously be used in a photovoltaic device 300 such as shown in FIG. 17. According to the optic functions encoded in the hologram, the device may or may not comprise a Fourier lens that makes it possible to reconstruct the hologram transmitted. The photovoltaic device 300 comprises a photovoltaic conversion element 302, for example one or several solar cells, arranged in the plane of reconstruction of the hologram, carrying out as such a photovoltaic conversion of the energy received in the form of the hologram. Contrary to the gas sensor application described hereinabove, the heating of the metal layer 112 of the emitting device 100 is not obtained by circulating an electric current through this layer or through the electrically conductive element 104, but by a solar radiation received by the device 100. Due to the fact that the metal layer 112 is sensitive over a broad spectrum, the latter is heated and then re-emits the energy according to a spectral output that is adapted to that of the photovoltaic conversion element 302, as such making it possible to improve the absorption of radiation by the photovoltaic conversion element 302. For this application, it is advantageous to encode an optic convergence function in the hologram, and/or by encoding the image of the photovoltaic conversion element 302 as a hologram, which optimises the return of energy on the photovoltaic conversion element 302.

The invention claimed is:

1. A light-emitting device comprising:
   a metal layer able to be heated and to propagate surface waves consecutive to the heating of the metal layer, the metal layer being structured such that the metal layer comprises several diffraction patterns able to carry out a diffraction of the surface waves to free-space propagation modes, wherein a synthetic hologram, able to control the form of a light radiation intended to be emitted by the light-emitting device via controlling the wavefront intended to be emitted, includes a plurality of pixels and is coded such that the synthetic hologram corresponds to a phase image coded in each of said plurality of pixels by an offset of the position of one of the diffraction patterns in relation to a reference position of said one of the diffraction patterns; and
   a heater of the metal layer.

2. The light-emitting device according to claim 1, wherein, in each of said plurality of pixels, the phase image is coded by an offset, along a first axis, of a position of said one of the diffraction patterns in relation to the reference position of said one of the diffraction patterns,
   wherein the reference positions of the diffraction patterns are defined as corresponding to intersections of a grid of n lines and of m columns regularly spaced from each other, the first axis being parallel to the n lines or to the m columns of the grid, wherein the diffraction patterns are regularly spaced from each other along a second axis perpendicular to the first axis, and
   wherein each offset in position of one of the diffraction patterns in relation to its reference position is less than a distance p that separates the two adjacent lines or two adjacent columns of the grid, with n and m integers greater than 1.

3. The light-emitting device according to claim 2, wherein the diffraction patterns have dimensions that are substantially similar in relation to each other, or wherein a relation between a dimension of each diffraction pattern according to the second axis and a dimension of said each diffraction pattern according to the first axis is greater than or equal to about 1.5, or
   wherein the diffraction patterns comprise openings made through at least a part of the thickness of the metal layer and a surface of a section of at least one of said openings of each diffraction pattern, in a main plane of the metal layer, is greater than or equal to about $p^2/2$.

4. The light-emitting device according to claim 1,
   wherein each diffraction pattern forms a part of a diffraction grating that comprises several slots parallel to one another,
   wherein, in each of said plurality of pixels, the phase image is encoded by an offset, along a first axis, of a position of the parts of the slots of said one of the diffraction patterns in relation to the reference position of said one of the diffraction patterns, and
   wherein the reference positions of the diffraction patterns are defined as corresponding to the positions wherein the parts of the slots of all of the diffraction patterns are aligned in relation to each other.

5. The light-emitting device according to claim 4, wherein the diffraction patterns comprise openings made through at least a part of the thickness of the metal layer.

6. The light-emitting device according to claim 1, wherein the heater of the metal layer comprises at least one electrically conductive element thermally coupled with the metal layer and able to be heated when an electric current passes through the at least one electrically conductive element.

7. The light-emitting device according to claim 1, further comprising
   a mechanical support element whereon is arranged the metal layer, or, when the heater of the metal layer comprises an electrically conductive element, an electric isolation element arranged between the electrically conductive element and the metal layer.

8. The light-emitting device according to claim 1, wherein the heater of the metal layer comprises
   at least one device able to circulate an electric current through the metal layer or,
   when said heater comprises an electrically conductive element, a device able to circulate an electric current through the electrically conductive element.

9. The light-emitting device according to claim 1, further comprising at least one Fourier lens arranged at a front focal distance from the metal layer and at a rear focal distance from a plane intended to receive the light emission from the device.

10. The light-emitting device according to claim 1, wherein a phase function of the synthetic hologram encoded in the metal layer comprises an optic function that is substantially similar to a convergence function of a Fourier lens.

11. The light-emitting device according to claim 1, wherein a phase function of the synthetic hologram encoded in the metal layer comprises an optic function able to compensate for a deformation of the light-emitting device during the heating of the metal layer.

12. The light-emitting device according to claim 1, wherein an image of the synthetic hologram is a slot.

13. A gas sensor comprising at least one light-emitting device according to claim 1 and a detector able to detect the presence of at least one gas in a space through which passes at least one image of the hologram emitted by the light-emitting device.

14. The gas sensor according to claim 13, wherein the detector is able to carry out a spectral detection of the image of the hologram at least in one range of wavelengths comprising at least one spectral absorption band of the gas or gases intended to be detected by the sensor.

15. The gas sensor according to claim 14, wherein the detector is able to carry out a spectral detection of several images of the hologram emitted by the light-emitting device in several ranges of wavelengths of which at least one comprises the spectral absorption band of the gas or gases intended to be detected by the sensor, or wherein the detector is able to carry out a spectral detection of a single image of the hologram emitted by the light-emitting device in a single range of wavelengths comprising the spectral absorption band of the gas intended to be detected by the sensor.

16. The gas sensor according to claim 13, wherein the detector comprises:
   a reflective element arranged facing the light-emitting device and able to reflect the image of the hologram that has passed through the space comprising the gas or gases towards the light-emitting device; and
   a device for measuring the electrical resistance of the metal layer or, when the heater of the metal layer comprises the electrically conductive element, a device for measuring the electrical resistance of the electrically conductive element.

17. A photovoltaic device comprising:
   at least one light-emitting device,
   wherein the light-emitting device comprises:
      a metal layer able to be heated and to propagate surface waves consecutive to the heating of the metal layer, the metal layer being structured such that it comprises several diffraction patterns able to carry out a diffraction of the surface waves to free-space propagation modes, wherein a synthetic hologram, able to control the form of a light radiation intended to be emitted by the light-emitting device via controlling the wavefront intended to be emitted, includes a plurality of pixels and is coded such that the synthetic hologram corresponds to a phase image coded in each of said plurality of pixels by an offset of the position of one of the diffraction patterns in relation to a reference position of said one of the diffraction patterns;
   wherein the metal layer of the light-emitting device is able to receive light rays received by the photovoltaic device, and
   wherein the photovoltaic device further comprises:
   at least one photovoltaic conversion element able to receive an image of the hologram intended to be emitted by the light-emitting device.

* * * * *